United States Patent

Fedorov et al.

[11] Patent Number: 5,856,120
[45] Date of Patent: Jan. 5, 1999

[54] METHOD OF PREPARING A BIOLOGICAL MATERIAL FOR USE IN OPHTHALMOLOGY

[75] Inventors: Svyatoslav Nikolayevich Fedorov; Sergei Nikolayevich Bagrov; Yevgeny Viktorovich Larionov; Vladimir Borisovich Malyshev, all of Moscow, Russian Federation

[73] Assignee: Staar Surgical Company, Inc., Monrovia, Calif.

[21] Appl. No.: 790,083

[22] Filed: Jan. 29, 1997

[51] Int. Cl.⁶ .............................. C12P 21/06; B29D 11/00
[52] U.S. Cl. .................. 435/68.1; 264/1.1; 264/1.38; 264/2.6; 264/28; 264/41; 351/160 H; 514/54; 530/356; 527/201; 523/105; 523/106; 523/108
[58] Field of Search .......................... 435/68.1; 623/4, 623/6; 514/54; 530/356; 523/105, 106, 108; 264/1.38, 2.6, 1.1, 28, 41; 351/160 H; 527/201

[56] References Cited

U.S. PATENT DOCUMENTS

| | | |
|---|---|---|
| Re. 33,997 | 7/1992 | Kuzma et al. . |
| 4,024,457 | 5/1977 | Kuettner et al. . |
| 4,064,008 | 12/1977 | Petersen et al. . |
| 4,220,724 | 9/1980 | Bert et al. . |
| 4,268,131 | 5/1981 | Miyata et al. ................... 351/160 H |
| 4,876,332 | 10/1989 | Tsilibary et al. . |
| 4,894,441 | 1/1990 | Menicagli . |
| 4,983,181 | 1/1991 | Civerchia ................................ 623/5 |
| 5,103,840 | 4/1992 | Kavoussi . |
| 5,104,957 | 4/1992 | Kelman et al. ........................ 527/201 |
| 5,210,182 | 5/1993 | Nasralish et al. . |
| 5,246,698 | 9/1993 | Leshchiner et al. .................... 514/54 |
| 5,424,408 | 6/1995 | Reeders et al. . |
| 5,476,515 | 12/1995 | Kelman et al. . |

*Primary Examiner*—Herbert J. Lilling
*Attorney, Agent, or Firm*—Klima & Pezzlo, P.C.

[57] ABSTRACT

A collagen containing substrate comprising cattle basal membrane is conditioned by incubating the membranes in a mixture of pepsin, hyaluronidase and acetic acid and separating the collagen from the mixture. The mixture can include pepsin, hyaluronidase and a 0.5M solution of acetic acid in 1:1:10 proportions. The incubation is conducted for about 10 hours at about 45° C. After incubation, collagen is separated from the mixture by centrifuging at a speed of 5000 to 30000 rpms for about 30 minutes. The collagen is mixed with polymerizable monomer and polymerized to form a gel that can be ground to form an intraocular or contact lens.

12 Claims, No Drawings

METHOD OF PREPARING A BIOLOGICAL MATERIAL FOR USE IN OPHTHALMOLOGY

FIELD OF THE INVENTION

The invention relates to a method for conditioning a collagen containing substrate to produce a biological material for use in ophthalmology.

BACKGROUND OF THE INVENTION

A polymeric biological material can be prepared by initial conditioning steps of enzyme treatment of animal raw material, such as pig sclera. Collagen is extracted from the raw material and is mixed with monomers for polymerization to ophthalmological materials, such as intraocular and contact lenses. The lenses are used for surgical or conservative treatment of myopia. The ophthalmological materials are also used to form collagen solutions for treating mild myopia and solutions to prepare external forms of medication.

There are a number of major deficiencies associated with this method. First, enzyme treatment with trypsin results in irreversible breakdown of the primary structure of pig sclera collagen. It is difficult to achieve high collagen concentrations in ophthalmological products manufactured from this collagen. Products manufactured from lower collagen concentrations are brittle.

It is an object of the invention to provide a collagen that can form high collagen concentrations.

It is another object of the invention to produce ophthalmological products that are not brittle.

It is still another object to condition a collagen containing substrate to provide a collagen that can be extensively used to produce strong, elastic intraocular lenses and contact lenses that are highly biocompatible and gas permeable.

SUMMARY OF THE INVENTION

The invention relates to a method for conditioning a collagen containing substrate. The method comprises steps of providing collagen containing cattle basal membrane, incubating the membrane in a mixture of pepsin, hyaluronidase and acetic acid and separating the collagen from the mixture. After conditioning, the collagen can be mixed with monomers and polymerized to produce strong, elastic intraocular lenses and contact lenses that are highly biocompatible and gas permeable.

DESCRIPTION OF THE INVENTION

Basal membrane is connective tissue and primarily consists of Type IV collagen. The collagen is non-fibrillar. The collagen is characterized by short structures and a molecular weight of 165 to 185,000. Cattle crystalline lenses, kidney capsules or placenta are sources of basal membrane. An anterior capsule is removed from the crystalline lens to be used as the collagen containing substrate. Placenta and other sources are physically cleaned to remove surface tissue. The resulting collagen containing substrate is rinsed with water. Weight of enzyme used and collagen precipitation speeds applied are determined on the basis of the type of collagen containing substrate. The collagen containing substrate is incubated in a 1:1:10 mixture of pepsin, hyaluronidase and 0.5M acetic acid solution for 10 hours at 45° C. Supernatant solution is drained from the incubated mixture and dialyzed and then the solution is centrifuged at a speed of 5000 to 30000 rpms for about 30 minutes.

The method of the invention provides a collagen that can be used to prepare a biological material for use in ophthalmology. The collagen content of the solution product is determined and the solution is mixed with a required proportion of polymerizable monomer and subjected to polymerization conditions in a mold to produce an ophthalmological product such as an intraocular or contact lens.

Type IV collagen is of a non-fibrillar, short-chain structure. Hence, the collagen of basal membrane can be easily incorporated with monomers into structures of polymers in very high concentrations up to 50%. It is believed that Type IV collagen imparts important biological properties to basal membrane including high gas-permeability, resistance to enzymes, strength and elasticity. Type IV collagen provides high transparency at high concentrations even in mixture with other biological polymers. Enzymatic hydrolysis does not disintegrate the primary structure of Type IV collagen. Further, basal membrane is a non-cellular structure that does not contain vessels. This makes basal membrane especially valuable for making biological material for ophthalmology. V. V. Serov, A. B. Shekhter, *Soyedinitelnaya tkan* (Connective Tissue), 1979, pp. 11–30.

According to the invention, basal membrane is physically extracted from cattle organs such as the crystalline lens, kidney and placenta. The cattle crystalline lens, kidney or placenta is cleaned to remove blood and particulate matter. The basal membrane is then incubated in the mixture of enzyme, pepsin and hyaluronidase and 0.5M solution of acetic acid in 1 to 1 to 10 proportions for the purpose of enzymatic and acid splitting. The pepsin hydrolyzes proteins to amino acids and the hyaluronidase hydrolyzes the collagen to a fibrillar state. The hydrolysis step is carried out for at least 10 hours at 45° C. to obtain complete hydrolysis. The hydrolysis step results in complete hydrolysis of all proteins, glycosaminoglycanes and other components of the membrane except the Type IV collagen. At 45° C., the enzymes are spontaneously inactivated after 10 hours. After hydrolysis, supernatant solution is drained and dialyzed. The solution is then centrifuged to separate the Type IV collagen. A centrifuging speed of 5000 rpms is satisfactory when the collagen content of the solution is high, while a speed of 30,000 rpms may be required for low collagen content solutions. A centrifuging time of 30 minutes at these speeds is adequate to separate all collagen.

The following examples are intended to illustrate the invention without limiting its scope.

EXAMPLE I

The following illustrates extraction of Type IV collagen from basal membrane from an anterior capsule of a cattle crystalline lens.

Crystalline lenses are extracted from cattle eyes and are placed in a physiologic solution to remove blood and vitreous enzyme residues. Anterior capsules are cut from the crystalline lenses with a sharp razor and the capsules are placed in an incubating enzyme solution. The enzyme solution contains 50 mg of pepsin, 50 mg of hyaluronidase and 500 ml of 0.5M acetic acid for 500 grams of capsules. The capsules (500 grams) are maintained in the solution for 10 hours at 45° C. with occasional stirring.

After 10 hours, a supernatant solution is drained from the enzyme solution and is centrifuged at 5000 rpms for 30 minutes to separate a collagen solution. The collagen solution is placed in dialysis bags and dialyzed with 0.05M acetic acid. The collagen concentration of the dialysate is determined. 70 grams of 2-hydroxy ethyl methacrylate is added to 10 grams of collagen and the mixture is thoroughly stirred and centrifuged at 3000 rpms for 30 minutes. The mixture is cooled to 4° C. and is exposed to 15 kilograms of radiation to produce a gel. The gel is dried and lenses are produced by grinding.

EXAMPLE II

The following illustrates extraction of Type IV collagen from basal membrane of cattle kidney capsules.

Cattle kidney capsules are thoroughly cleaned to remove blood and impurities. The capsules are cut with a razor and the capsules are homogenized in a Potter homogenizer. The capsules are then placed in an incubating enzyme solution. The enzyme solution contains 10 mg of pepsin, 100 mg of hyaluronidase and 1 liter of 0.5M acetic acid for 1 kilogram of capsules. The capsules (1 kilogram) are maintained in the solution for 10 hours at 45° C. with occasional stirring.

After 10 hours, a supernatant is drained from the enzyme solution and is centrifuged at 10000 rpms for 30 minutes to separate collagen. The collagen is dialyzed with 0.05M acetic acid. The collagen concentration of the dialysate is determined. 50 grams of acrylamide with 0.01 gram of N-methylene bisacrylamide and water is added to 10 grams of collagen. The resulting gel is placed into a mold, cooled to 0° C. and exposed to 5 kilograys of gamma irradiation. The molded gel is dried and ground into lenses.

EXAMPLE III

The following illustrates extraction of Type IV collagen from basal membrane of cattle placenta.

Cattle placenta is physically cleaned and homogenized in a Potter homogenizer. Homogenate (1 kilogram) is placed in an incubating solution of 100 mg of pepsin and 100 mg of hyaluronidase in 1 liter of a 0.5M solution of acetic acid for 10 hours at 45° C.

After 10 hours, a supernatant is drained from the enzyme solution and is centrifuged at 30000 rpms for 30 minutes to separate a collagen. The collagen is placed in dialysis bags and dialyzed with 0.05M acetic acid. The collagen concentration of the dialysate is determined. 70 grams of 2-hydroxy methacrylate is added to 10 grams of collagen. The resulting mixture is thoroughly stirred and centrifuged at 3000 rpms for 30 minutes. The mixture is cooled to 4° C. and is exposed to 15 kilograys of radiation to produce a gel. The gel is dried and lenses are produced from the dried gel by grinding.

Other modifications of the present invention will occur to those skilled in the art subsequent to a review of the present application. These modifications and equivalents are intended to be included within the scope of the invention.

What is claimed:

1. A method of forming a collagen containing substrate gel, comprising the steps of:
    providing collagen containing cattle basal membranes;
    incubating said membranes in a mixture of pepsin, hyaluronidase and acetic acid; separating collagen from said mixture; and
    forming a mixture of polymerizable monomer and said separated collagen and polymerizing said mixture to form a gel.

2. The method of claim 1, comprising cleaning said cattle basal membranes prior to said incubating step.

3. The method of claim 1, comprising incubating said membranes in a mixture of pepsin, hyaluronidase and a 0.5M solution of acetic acid in about 1:1:10 proportions.

4. The method of claim 3, comprising incubating said membranes for about 10 hours at about 45° C.

5. The method of claim 1, comprising separating said collagen from said mixture by centrifuging.

6. The method of claim 5, comprising separating said collagen from said mixture by centrifuging at a speed of 5000 to 30000 rpms for about 30 minutes.

7. The method of claim 1, including drying said gel and grinding dried gel to form an ophthalmological product.

8. The method of claim 7, wherein said ophthalmological product is an intraocular lens.

9. The method of claim 7, wherein said ophthalmological product is a contact lens.

10. The method of claim 1, wherein radiation is applied to said mixture to facilitate polymerization of said mixture.

11. The method of claim 1, wherein said monomer is one selected from the group consisting of 2-hydroxy ethyl methacrylate, acrylamide, and 2-hydroxy acrylate.

12. A method of forming a collagen containing substrate gel, comprising the steps of:
    providing collagen containing cattle basal membranes;
    incubating said membranes in a mixture of pepsin, hyaluronidase and acetic acid;
    separating collagen from said mixture; and
    forming a mixture of polymerizable monomer and said separated collagen and polymerizing said mixture to form a gel, said monomer being one selected from the group consisting of 2-hydroxy ethyl methacrylate, acrylamide, and 2-hydroxy acrylate.

* * * * *

UNITED STATES PATENT AND TRADEMARK OFFICE
CERTIFICATE OF CORRECTION

PATENT NO. : 5,856,120
DATED      : January 5, 1999
INVENTOR(S) : Svyatoslav Nikolayevich Fedorov, et al.

It is certified that error appears in the above-identified patent and that said Letters Patent is hereby corrected as shown below:

On the title page, item [73]:
    Assignee: change "STAAR Surgical Company, Inc.; Monrovia, Calif." to --STAAR Surgical AG; Switzerland--.

Signed and Sealed this

Twenty-first Day of March, 2000

Attest:

Q. TODD DICKINSON

Attesting Officer

Commissioner of Patents and Trademarks